(12) United States Patent
He et al.

(10) Patent No.: US 10,440,957 B2
(45) Date of Patent: Oct. 15, 2019

(54) ROOTING AGENT FOR WOODY PLANTS CUTTING

(71) Applicant: Yibin Yunchen Abor & Gargen Co., Ltd., Yibin, Sichuan (CN)

(72) Inventors: Sufen He, Sishuan (CN); Li Zhong, Sichuan (CN); Jing Yang, Sichuan (CN); Hua Wu, Sichuan (CN); Lidong Qiao, Sichuan (CN); Xuemei Jian, Chongqing (CN); Lei Li, Sichuan (CN)

(73) Assignee: Yibin Yunchen Abor & Gargen Co., Ltd., Yibin, Sichuan (CN)

( * ) Notice: Subject to any disclaimer, the term of this patent is extended or adjusted under 35 U.S.C. 154(b) by 0 days.

(21) Appl. No.: 15/561,068

(22) PCT Filed: Dec. 29, 2016

(86) PCT No.: PCT/CN2016/113059
§ 371 (c)(1),
(2) Date: Sep. 24, 2017

(87) PCT Pub. No.: WO2017/173860
PCT Pub. Date: Oct. 12, 2017

(65) Prior Publication Data
US 2018/0184665 A1    Jul. 5, 2018

(30) Foreign Application Priority Data

Apr. 8, 2016   (CN) .......................... 2016 1 0215291

(51) Int. Cl.
| | | |
|---|---|---|
| A01N 59/16 | (2006.01) | |
| A01N 59/14 | (2006.01) | |
| A01N 43/08 | (2006.01) | |
| A01N 47/28 | (2006.01) | |
| A01N 31/08 | (2006.01) | |
| A01N 37/10 | (2006.01) | |
| C05G 3/02 | (2006.01) | |
| C05G 3/00 | (2006.01) | |
| A01G 2/10 | (2018.01) | |
| A01N 47/14 | (2006.01) | |
| A01N 25/02 | (2006.01) | |
| A01N 37/18 | (2006.01) | |
| A01N 43/76 | (2006.01) | |
| C05C 9/00 | (2006.01) | |

(52) U.S. Cl.
CPC ............... *A01N 59/16* (2013.01); *A01G 2/10* (2018.02); *A01N 31/08* (2013.01); *A01N 37/10* (2013.01); *A01N 43/08* (2013.01); *A01N 43/76* (2013.01); *A01N 47/14* (2013.01); *A01N 47/28* (2013.01); *A01N 59/14* (2013.01); *C05C 9/005* (2013.01); *C05G 3/00* (2013.01); *C05G 3/02* (2013.01); *A01N 25/02* (2013.01); *A01N 37/18* (2013.01); *A01N 2300/00* (2013.01)

(58) Field of Classification Search
CPC ........ A01N 59/16; A01N 37/18; A01N 25/02; A01N 2300/00; A01N 43/76; A01N 43/08; A01N 47/28; A01N 31/08; A01N 37/10; A01N 59/14; A01N 47/14; A01G 2/10; C05G 3/02; C05G 3/00; C05C 9/005
See application file for complete search history.

(56) References Cited

FOREIGN PATENT DOCUMENTS

| CN | 101397221 A | * | 4/2009 |
| CN | 105859406 A |   | 8/2016 |

OTHER PUBLICATIONS

CN105859406, 2016, English Translation, Patent Translate Powered by EPO and Google, 7 pages. (Year: 2016).*
CN101397221, 2009, English Translation, Patent Translate Powered by EPO and Google, 8 pages. (Year: 2009).*
Chen et al., CN102675001 Derwent Abstract, 2012, Derwent Abstracts, 4 pages. (Year: 2012).*
Wang, S., CN103524155 Derwent Abstract, 2014, Derwent Abstracts, 3 pages. (Year: 2014).*
Cheng Y. et al., CN101508611, 2009, Derwent Abstracts, 4 pages. (Year: 2009).*

* cited by examiner

*Primary Examiner* — John Pak
*Assistant Examiner* — Andriae M Holt

(57) ABSTRACT

A rooting agent for woody plants cutting includes raw materials of: sodium naphthalene-1-acetate, naphthalene acetamide, catechol, vitamin C, oxadixyl-mancozeb, boric acid, white sugar and urea. The rooting agent of the present invention contains various beneficial substances and rich nutrients and is easy absorbing. The rooting agent is capable of effectively improving rooting rate of woody plants cutting, and plants which are difficult to root has a high rooting rate after applying the rooting agent.

8 Claims, No Drawings

ROOTING AGENT FOR WOODY PLANTS CUTTING

CROSS REFERENCE OF RELATED APPLICATION

This is a U.S. National Stage under 35 U.S.C. 371 of the International Application PCT/CN2016/113059, filed Dec. 29, 2016, which claims priority under 35 U.S.C. 119(a-d) to CN 201610215291.5, filed Apr. 8, 2016.

BACKGROUND OF THE PRESENT INVENTION

Field of Invention

The present invention relates to the field of a plant growth regulator and an asexual reproduction technique, and more particularly to a rooting agent for woody plants cutting.

Description of Related Arts

Garden plant production cannot be separated from seeding breeding. In general, the seeding breeding includes sexual breeding such as by seed and asexual breeding such as grafting and cutting. However, in sexual breeding, some plants almost have no seed generated such as Michelia champaca and Biond Magnolia Flower; some plants produce very small number of seeds or seeds with an extremely low germination percentage, such as Liriodendron chinense and Manglietia insignis. In addition, the seeding plants which are bred by seeds have large variability and are easy to make plants loose excellent characteristics. When grafting is utilized for breeding, some plants have low survival rate. In addition, grating requires high technology and a low breeding coefficient, such as Camellia oleifera and Oriental cherry, and it is difficult for the grating to meet the demands of the garden industry. Cutting breeding not only is conducive to rapidly breed large quantities of seedlings, but also maintains the original excellent characteristics of plants. However, it is extremely difficult for some plants to root during cutting breeding, such as Pistacia chinensis and Machilus, which also affects the seeding breeding and production development.

With the promotion and application of plant growth regulators in agriculture and forestry production, the rooting rate of many commonly used plant cuttings are effectively improved. However, the use of a single growth regulator does not work or has a poor effect on the hard rooting plants, furthermore, the absorption effect of the growth regulator is also a problem.

SUMMARY OF THE PRESENT INVENTION

In view of the problems mentioned above, the present invention provides a rooting agent for woody plants cutting, which is capable of effectively improving rooting rate of woody plants cutting, in such a manner the rooting rate of the general woody plant cutting increases to 95%-100% and the rooting rate of plants which are difficult to root reaches 50-80% or above.

Accordingly, in order to achieve the objects mentioned above, the present invention adopts technical solutions as follows.

A rooting agent for woody plants cutting, comprising raw materials of: sodium naphthalene-1-acetate, naphthalene acetamide, catechol, vitamin C, oxadixyl-mancozeb, boric acid, white sugar and urea.

Furthermore the raw materials respectively account for parts by weight of: 0.05-0.15 part of sodium naphthalene-1-acetate; 0.01-0.1 part of naphthalene acetamide; 0.01-0.1 part of catechol; 0.01-0.05 part of vitamin C; 0.1-0.5 part of oxadixyl-mancozeb; 0.02-0.05 part of boric acid; 1.5-2.5 parts of white sugar; 0.5-1 part of urea and 1000 parts of water.

Furthermore, the raw materials respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water.

Preferably, the oxadixyl-mancozeb is a mixture of mancozeb and oxadixyl, and accounting by weight part, mancozeb: oxadixyl=1:3-4.5.

Preferably, accounting by weight part, in the oxadixyl-mancozeb, mancozeb: oxadixyl=1:4.

Beneficial effects of the present invention are as follows.

1. Both sodium naphthalene-1-acetate and naphthalene acetamide are plant-growth accelerator. When the sodium naphthalene-1-acetate and naphthalene acetamide are absorbed by the stem or leaf of the plant, the conduction is slow, so as to promote stimulating callus differentiation on a low end of the cutting shoot and formation of root primordium, so as to promote the cutting shoot to generate adventitious roots. The effect of mixing the sodium naphthalene-1-acetate and naphthalene acetamide is better than using them separately.

2. Catechol is a strong reducer. Since hydroquinone is capable of effectively inhibiting biological activity of IAA oxidase (indole acetic acid oxidase) in the stem cutting, in such a manner that exogenous treated auxin is capable of fully playing its role in rooting, so the rooting promoting effect is good. The mixing usage of the sodium naphthalene-1-acetate, naphthalene acetamide and catechol has a significant synergistic effect.

3. Vitamin C is involved in the reduction oxidation effect of the electron transfer system in the plant. Being a strong reducing agent or electron donor, vitamin C is capable of promoting metabolism, removing active oxygen in the body of the plant, delaying the aging of the plant, so as to promote rooting of the stem cutting.

4. Oxadixyl-mancozeb is a complex of fungicides with apparent effect, a main ingredient thereof is mancozeb and oxadixyl. Oxadixyl-mancozeb at the same time has two excellent characteristics of pesticides. Oxadixyl, which is a heterocyclic compound, is a kind of internal fungicides and disinfectants. Mancozeb is not only a fungicide, but also a plant growth regulator. Mancozeb is not only capable of inhibiting normal growth of mycelium of pathogenic bacteria, directly killing the bacteria, but also providing the plant cutting with trace elements of manganese and zinc. By combing mancozeb and oxadixyl to form oxadixyl-mancozeb, the sterilizing effect of oxadixyl is utilized and the systemic effect thereof is utilized as well, so as to ensure that mancozeb is better absorbed; meanwhile, the systemic effect of the oxadixyl also ensures that other beneficial substances are better absorbed.

5. Boric acid: Boron trace elements are contained therein. Boron is involved in the operation of plant sugar and metabolism and synthesis of protein, so as to promote the cutting rooting and growth and development of the roots.

6. Sugar and urea: Plant cuttings rooting needs some nutrients, the nutrients have great significance on the original body differentiation, especially carbohydrates and nitrogen compounds. Sugar is an indispensable carbon source for plant cutting and provides cells with carbon skeleton for the synthesis of new compounds; and provides substrate and energy for cell respiratory metabolism and also maintains a certain osmotic pressure. Urea contains high nitrogen, wherein nitrogen is called the life element and is the composition of amino acid and the composition of the protein. Treating the rooting cutting with sugar and urea is capable of effectively providing the callus differentiation and root formation with the necessary nutrients material, so as to promote the rooting effect of cuttings.

7. By combing plant growth agents and cofactor complex, combining functional substances, organic matter, inorganic nutrients, trace elements and fungicides in one body, a strong quick-acting rooting agent is combined. The strong quick-acting rooting agent contains antiviral and anti-aging factor of the quick rooting factor, can be absorbed through the stem and leaf into the plant body, so as stimulate the activity of the enzyme to promote the rapid formation of root radicals. After being applied for 20-25 days, easy rooting plants can be induced to generate new root system; and being applied for 25-30 days, hard rooting plants can be induced to generate new root system. Meanwhile, the present invention overcomes the cutting failure caused by bacteria invasion rot. The product of the present invention has a low cost, simple preparation, easy utilization, strong disease resistance, fast rooting and high survival rate.

8. The product of the present invention has a simple composition, easy operation, low cost, and is suitable for self-employed entrepreneurs, community, garden company and forestry production units.

These and other objectives, features, and advantages of the present invention will become apparent from the following detailed description, the accompanying drawings, and the appended claims.

DETAILED DESCRIPTION OF THE PREFERRED EMBODIMENT

In order to further illustrate the intended objects, the technical solutions and the efficiency, detailed description of the present invention is illustrated combining with the preferred embodiments of the present invention.

EXAMPLE 1

A rooting agent for woody plants cutting, raw materials of the rooting agent respectively account for parts by weight of: 0.05 part of sodium naphthalene-1-acetate; 0.1 part of naphthalene acetamide; 0.01 part of catechol; 0.01 part of vitamin C; 0.1 part of oxadixyl-mancozeb; 0.02 part of boric acid; 1.5 parts of white sugar; 0.5 part of urea and 1000 parts of water. A base portion of cutting shoot of excoecaria cochinchinensis is soaked for 1 hour, and rooting appears after 20 days of the cottage. 25-day rooting rate reaches 100%. The oxadixyl-mancozeb is a mixture of mancozeb and oxadixyl. Accounting by weight, mancozeb: oxadixyl=1:3.

EXAMPLE 2

A rooting agent for woody plants cutting, raw materials of the rooting agent respectively account for parts by weight of: 0.15 part of sodium naphthalene-1-acetate; 0.01 part of naphthalene acetamide; 0.1 part of catechol; 0.05 part of vitamin C; 0.5 part of oxadixyl-mancozeb; 0.02 part of boric acid; 2.5 parts of white sugar; 1 part of urea and 1000 parts of water. A base portion of cutting shoot of Acer rubrum is soaked for 1.5 hours, and rooting appears after 20 days of the cottage. 25-day rooting rate reaches 95%. The oxadixyl-mancozeb is a mixture of mancozeb and oxadixyl. Accounting by weight, mancozeb: oxadixyl=1:4.5.

EXAMPLE 3

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water. A base portion of cutting shoot of Prunus cerasifera is soaked for 2 hours, and rooting appears after 25 days of the cottage. 35-day rooting rate reaches 85%. The oxadixyl-mancozeb is a mixture of mancozeb and oxadixyl. Accounting by weight, mancozeb: oxadixyl=1:4.

EXAMPLE 4

A rooting agent for woody plants cutting, raw materials of the rooting agent respectively account for parts by weight of: 0.15 part of sodium naphthalene-1-acetate; 0.03 part of naphthalene acetamide; 0.04 part of catechol; 0.02 part of vitamin C; 0.2 part of oxadixyl-mancozeb; 0.02 part of boric acid; 1.8 parts of white sugar; 0.8 part of urea and 1000 parts of water. A base portion of cutting shoot of Manglietia insignis is soaked for 2 hours, and rooting appears after 30 days of the cottage. 35-day rooting rate reaches 50%. The oxadixyl-mancozeb is a mixture of mancozeb and oxadixyl. Accounting by weight, mancozeb: oxadixyl=1:3.5.

EXAMPLE 5

A rooting agent for woody plants cutting, raw materials of the rooting agent respectively account for parts by weight of: 0.05 part of sodium naphthalene-1-acetate; 0.1 part of naphthalene acetamide; 0.08 part of catechol; 0.01 part of vitamin C; 0.4 part of oxadixyl-mancozeb; 0.02 part of boric acid; 2.5 parts of white sugar; 0.6 part of urea and 1000 parts of water. A base portion of cutting shoot of Yulan magnolia is soaked for 2 hours, and rooting appears after 25 days of the cottage. 25-day rooting rate reaches 70%. The oxadixyl-mancozeb is a mixture of mancozeb and oxadixyl. Accounting by weight, mancozeb: oxadixyl=1:4.2.

EXAMPLE 6

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water. A base portion of cutting shoot of camellia is soaked for 2 hours, and rooting appears after 30 days of the cottage. 35-day rooting rate reaches 65%. The oxadixyl-mancozeb is a mixture of mancozeb and oxadixyl. Accounting by weight, mancozeb: oxadixyl=1:4.

EXAMPLE 7

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water.

A base portion of cutting shoot of Flowering cherry is soaked for 1.5 hours, and rooting appears after 30 days of the cottage. 35-day rooting rate reaches 75%. The oxadixyl-mancozeb is a mixture of mancozeb and oxadixyl. Accounting by weight, mancozeb: oxadixyl=1:4.

EXAMPLE 8

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water. A base portion of cutting shoot of Liriodendron chinese is soaked for 1 hour, and rooting appears after 25 days of the cottage. 35-day rooting rate reaches 80%. The oxadixyl-mancozeb is a mixture of mancozeb and oxadixyl. Accounting by weight, mancozeb: oxadixyl=1:4.

EXAMPLE 9

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water. A base portion of cutting shoot of Olive is soaked for 1 hour, and rooting appears after 20 days of the cottage. 25-day rooting rate reaches 80%. The oxadixyl-mancozeb is a mixture of mancozeb and oxadixyl. Accounting by weight, mancozeb: oxadixyl=1:4.

EXAMPLE 10

A rooting agent for woody plants cutting, raw materials of the rooting agent respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water. A base portion of cutting shoot of Photinia glabra is soaked for 1 hour, and rooting appears after 20 days of the cottage. 25-day rooting rate reaches 97%. The oxadixyl-mancozeb is a mixture of mancozeb and oxadixyl. Accounting by weight, mancozeb: oxadixyl=1:4.5.

COMPARATIVE EXAMPLE

Rooting agent for woody plants cutting is prepared according to the methods of the examples 1-10. The methods are different in that a first type is a rooting agent ingredient mainly containing sodium naphthalene-1-acetate and naphthalene acetamide; and a second type is a rooting agent ingredient by adding different concentrations of catechol under conditions of an identical concentration of sodium naphthalene-1-acetate and naphthalene acetamide with the first type, so as to prepare the rooting agents in the comparative examples 1-10. With identical dosage applied, the two types of rooting agent are respectively soaked with cutting shoot of a same plant; and cutting management is performed under identical temperature and humidity. Effects of different rooting agents on rooting of cutting plants are counted, and results are shown in Table. 1.

It can be seen from Table. 1 that for the rooting agent for woody plants cutting of the present invention, when the sodium naphthalene-1-acetate, naphthalene acetamide and the catechol are utilized in combination, significant synergistic effects are appeared, and the rooting rate us significantly improved.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A rooting agent for woody plants cutting, comprising raw materials of: sodium naphthalene-1-acetate, naphthalene acetamide, catechol, vitamin C, oxadixyl-mancozeb, boric acid, white sugar and urea, wherein the oxadixyl-mancozeb is a mixture of mancozeb and oxadixyl;

wherein the raw materials respectively account for parts by weight of: 0.05-0.15 part of sodium naphthalene-1-acetate; 0.01-0.1 part of naphthalene acetamide; 0.01-0.1 part of catechol; 0.01-0.05 part of vitamin C; 0.1-0.5 part of oxadixyl-mancozeb; 0.02-0.05 part of boric acid; 1.5-2.5 parts of white sugar; 0.5-1 part of urea and 1000 parts of water.

2. The rooting agent for woody plants cutting, as recited in claim 1, wherein the raw materials respectively account for parts by weight of: 0.1 part of sodium naphthalene-1-acetate; 0.06 part of naphthalene acetamide; 0.05 part of catechol; 0.03 part of vitamin C; 0.3 part of oxadixyl-mancozeb; 0.03 part of boric acid; 2 parts of white sugar; 0.7 part of urea and 1000 parts of water.

3. The rooting agent for woody plants cutting, as recited in claim 2, wherein the oxadixyl-mancozeb is a mixture of mancozeb and oxadixyl, and accounting by weight part, mancozeb: boxadixyl=1:3-4.5.

4. The rooting agent for woody plants cutting, as recited in claim 1, wherein the oxadixyl-mancozeb is a mixture of mancozeb and oxadixyl, and accounting by weight part, mancozeb: oxadixyl=1:3-4.5.

5. The rooting agent for woody plants cutting, as recited in claim 1, wherein in the oxadixyl-mancozeb, and accounting by weight part, mancozeb: oxadixyl=1:4.

6. The rooting agent for woody plants cutting, as recited in claim 2, wherein in the oxadixyl-mancozeb, and accounting by weight part, mancozeb: oxadixyl=1:4.

7. A rooting agent for woody plants cutting, comprising raw materials of: 0.05 part by weight of sodium naphthalene-1-acetate; 0.1 part by weight of naphthalene acetamide; 0.01 part by weight of catechol; 0.01 part by weight of vitamin C; 0.1 part by weight of oxadixyl-mancozeb; 0.02 part by weight of boric acid; 1.5 parts by weight of white sugar; 0.5 part by weight of urea and 1000 parts by weight of water, wherein the oxadixyl-mancozeb is a mixture of mancozeb and oxadixyl and accounting by weight, mancozeb: oxadixyl=1:3.

8. A rooting agent for woody plants cutting, comprising raw materials of: 0.1 part by weight of sodium naphthalene-1-acetate; 0.06 part by weight of naphthalene acetamide; 0.05 part by weight of catechol; 0.03 part of vitamin C; 0.3 part by weight of oxadixyl-mancozeb; 0.03 part by weight of boric acid; 2 parts by weight of white sugar; 0.7 part by weight of urea and 1000 parts by weight of water, wherein the oxadixyl-mancozeb is a mixture of mancozeb and oxadixyl and accounting by weight, mancozeb: oxadixyl=1:4.5.

\* \* \* \* \*